(12) United States Patent
Niemczyk

(10) Patent No.: US 6,518,254 B1
(45) Date of Patent: Feb. 11, 2003

(54) RIBONUCLEOSIDE-TRIBOSE

(76) Inventor: Henry Joseph Niemczyk, 50 Wilson Ave., Wayne, NJ (US) 07470

( * ) Notice: Subject to any disclaimer, the term of this patent is extended or adjusted under 35 U.S.C. 154(b) by 0 days.

(21) Appl. No.: 10/120,229

(22) Filed: Apr. 11, 2002

(51) Int. Cl.[7] ...................... A61K 31/70; A01N 43/647; A01N 43/64

(52) U.S. Cl. ........................ 514/43; 514/42; 536/1.11; 536/18.7; 536/22.1; 536/26.9; 536/55.3; 536/124

(58) Field of Search .................... 514/43, 42; 536/1.11, 536/18.7, 22.1, 26.9, 55.3, 124

(56) References Cited

PUBLICATIONS

Sidwell et al., Science 177, 705 (1972).*

* cited by examiner

*Primary Examiner*—Samuel Barts
*Assistant Examiner*—Michael C. Henry

(57) ABSTRACT

The present invention is a novel Ribonucleoside TRIBOSE. A process to prepare the nucleoside is also disclosed. The Ribonucleoside is a new chemical entity (NCE) not previously described. The preparation of the nucleoside portion of the molecule, also not previously described involves a thermal rearrangement of 3-Isoxazolecarboxylic acid, 5-methyl-,2-(phenylmethyl)-hydrazide, The resulting 1,2,3 ribonucleoside has anti-viral and anti-neoplastic activity potential.

4 Claims, 4 Drawing Sheets

1
TRIBOSE

1A

RIBONUCLEOSIDE-TRIBOSE

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

Ribonucleosides such as Ribavirin have been used as antivirals independently and in combination with other drugs for many years. Ribavirin, 1-beta-D-ribofuranosyl-1H-1,2,4-triazole-3-carboxamide, has a carboxamide substituent on a 1,2,4 triazole ring. The antiviral spectrum for Ribavirin was the first broad band antiviral, which did not induce interferon. In invitro tissue culture it was demonstrated to be active against at least 16 DNA and RNA viruses. (Science, 177, 705, 1972). More recently, the L isomer of Ribavirin has shown immuno-modulatory activity similar to Ribavirin but with a better tolerability profile. Phase I clinical trials were initiated in February 2001.

Ribonucleosides also have the potential as therapeutic agents in oncology, since they target mRNA resulting in the prevention of gene translation. Additionally, there is a potential therapeutic application in the treatment of ocular diseases. TRIBOSE can be considered the next generation ribonucleoside.

A significant differentiation between TRIBOSE and Ribavirin is in the triazole ring structure. Ribavirin contains a 1,2,4 triazole ring whereas TRIBOSE contains a 1,2,3 triazole ring. Other key differences are with different substitutents on the triazole ring. A 1,2,3-triazole ribonucleoside, (TRIBOSE), has not been tested for pharmacological activity either with specific targets or in general. The present invention is such a triazole. Not only has the Ribonucleoside described never been previously synthesized or tested, the nucleoside itself is not described in the literature. Although it is prepared from known and commercially available materials and the synthesis of the key intermediate 3-Isoxazolecarboxylic acid, 5-methyl-,2-(phenylmethyl)-hydrazide has been a commercial drug for many years and marketed around the world as an antidepressant, the nucleoside prepared from it has not been tested for pharmacological activity.

The final chemical step of the process to prepare this nucleoside is also one of the claims of the present invention. It is a thermal isomerization of 5-Methyl-3-isoxazolecarboxylic acid 2-(phenylmethyl) hydrazide to form the 1,2,3 triazole as shown in FIG. 2.

In addition to potential anti-viral activity, its potential for anti-neoplastic activity, TRIBOSE 1 can be viewed as an anti-sense drug. Altering the activity of the target RNA or interference with replication on a cellular level can include several mechanisms. One may be the steric hindrance resulting from the substituants on the triazole ring. A second can be due to the hydroxy function, which because of its relationship with the hydroxy function of ribose can mimic ribose and interfere with replication. The hydroxy function on the triazole ring is also subject to phosphorylation, which can enhance the antitumor activity. The similarity of the five membered ring of the triazole and the five membered ring of ribose also has the potential to interfere with the fusion reaction between DNA and mRNA. These are but three examples of how TRIBOSE can potentially interfere on a cellular level with the replication of viruses and or tumors. A significant difference between Ribavirin and TRIBOSE is in the symmetry of TRIBOSE having a 1,2,3-triazole ring as opposed to the 1,2,4-triazole ring of Ribavirin.

By having the potential to mimic the biochemical activity of nucleic acids, TRIBOSE and its derivatives enter into a cell's nucleic acid, namely RNA and DNA, and do not permit the continuance of nucleic acid synthesis which accounts for their effectiveness. Because of the potential toxic effects to normal cells, administration by direct infusion into the tumor has the potential for maximum effectiveness with minimal side effects.

This invention relates to the novel Ribonucleoside TRIBOSE and derivatives of TRIBOSE as depicted in FIG. 4 where R1, R2, and R3 represent alkyl, acyl, hydroxy, keto, amino, phenyl, and the like. Synthesis and evaluation of TRIBOSE analogs have the potential to obtain a target molecule, which is more effective, less toxic and better tolerated than TRIBOSE. The optimum TRIBOSE candidate would target cancerous cells while leaving normal cells unchanged.

In addition to potential increased efficacy and tolerability, a key advantage of TRIBOSE as compared to other Ribonucleosides is the relative ease of synthesis. Although it is a multi-step synthesis, it is not overly complicated, has well defined intermediates obtained in good yields and are stable. Overall, substantial quantities of TRIBOSE can be readily prepared.

BRIEF SUMMARY OF THE INVENTION

FIG. 1 depicts the final chemical reaction step to produce TRIBOSE 1. Reacting a protected Ribose, having structure 3 with the triazole, having structure 2 to form the Ribonucleoside, followed by deprotection, to form structure 1 has been carried out in similar reactions such as Ribavirin.(J T Witkowski et al., J Med. Chem. 15, 1150, 1972). The reaction can be carried out either chemically or enzymatically. The present invention is the new chemical entity represented by structure 1 in FIG. 1. Claim 2 of the present invention is the preparation of compound having the structure 2 represented in FIG. 1. The preparation of 2 is depicted in FIG. 2. The isomeric rearrangement of compound 4 to form compound 2 can be carried out neat or in a solvent near the melting point of compound 4. Compound 4, 3-Isoxazolecarboxylic acid, 5-methyl-,2-(phenylmethyl)-hydrazide, has been marketed as an antidepressant for many years and its preparation on a commercial scale is known, and is shown as part of FIG. 3. Once it was discovered that compound 4 could be thermally isomerized to the 1,2,3 triazole having the structure 2, several experiments were conducted under various temperatures to optimize its formation. Once produced, the material was identified through elemental analysis, mass spectroscopy, and NMR. Although not fully optimized, enough material was produced to demonstrate the practicality of producing it via a thermal isomerization.

BRIEF DESCRIPTION OF THE DRAWING

The drawings depicted in FIG. 1 represent the reaction between the protected ribose 3 and the triazole 2 to form the ribonucleoside which is then deprotected to form 1.

The drawings depicted in FIG. 2 represent the thermal isomerization to form the triazole 2 from structure 4.

Figure 1:
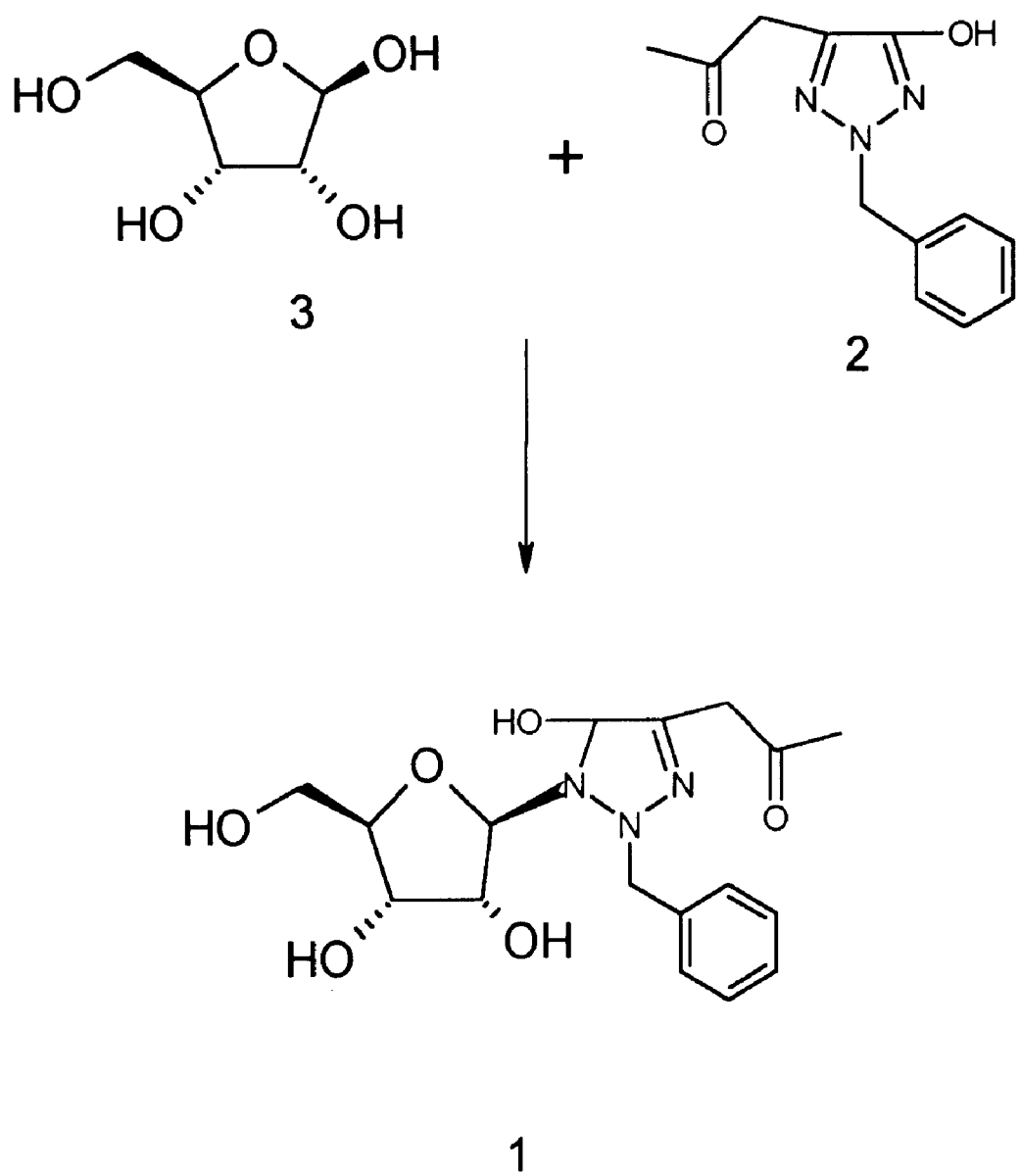
Figure 2:
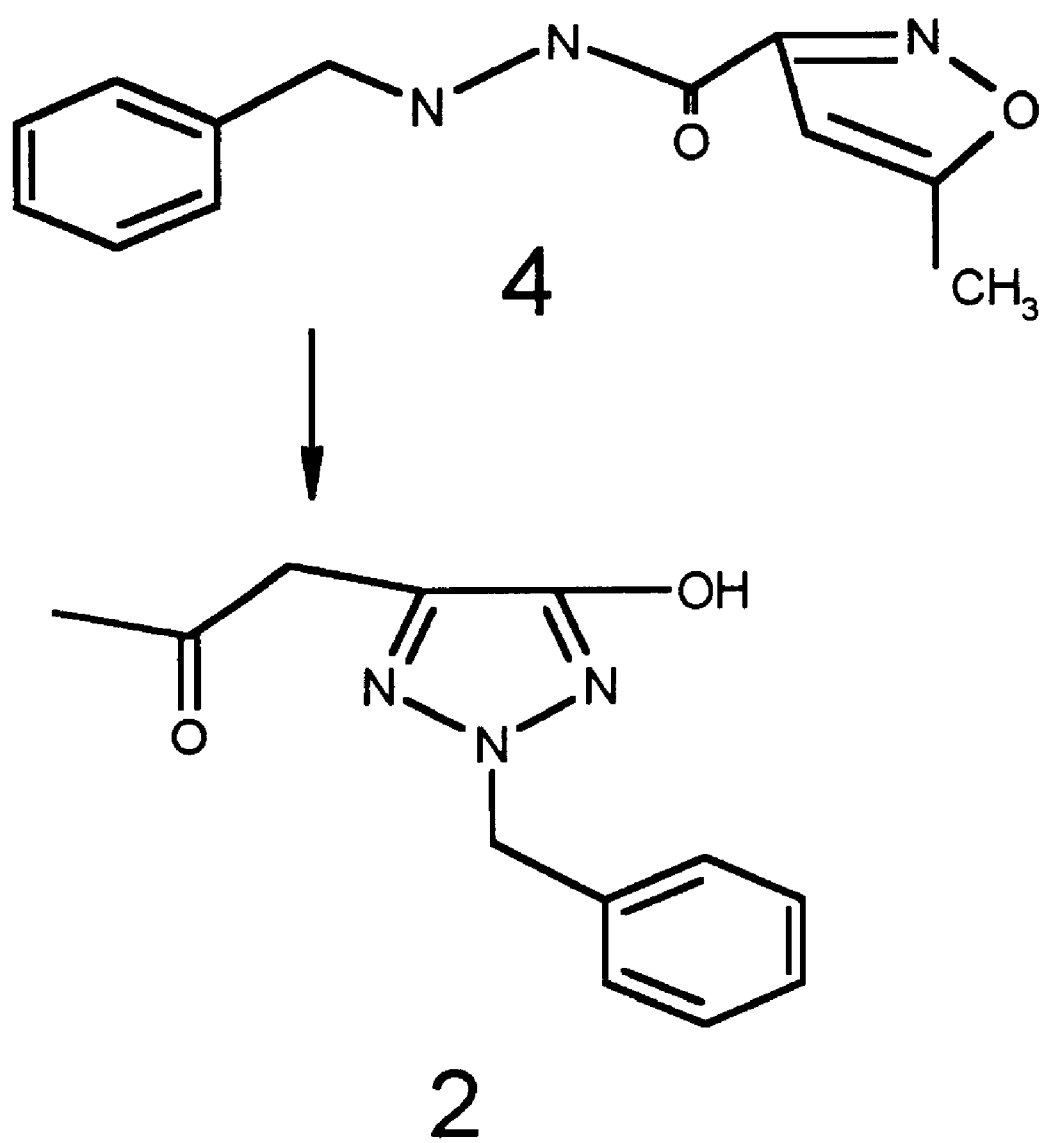
Figure 3:
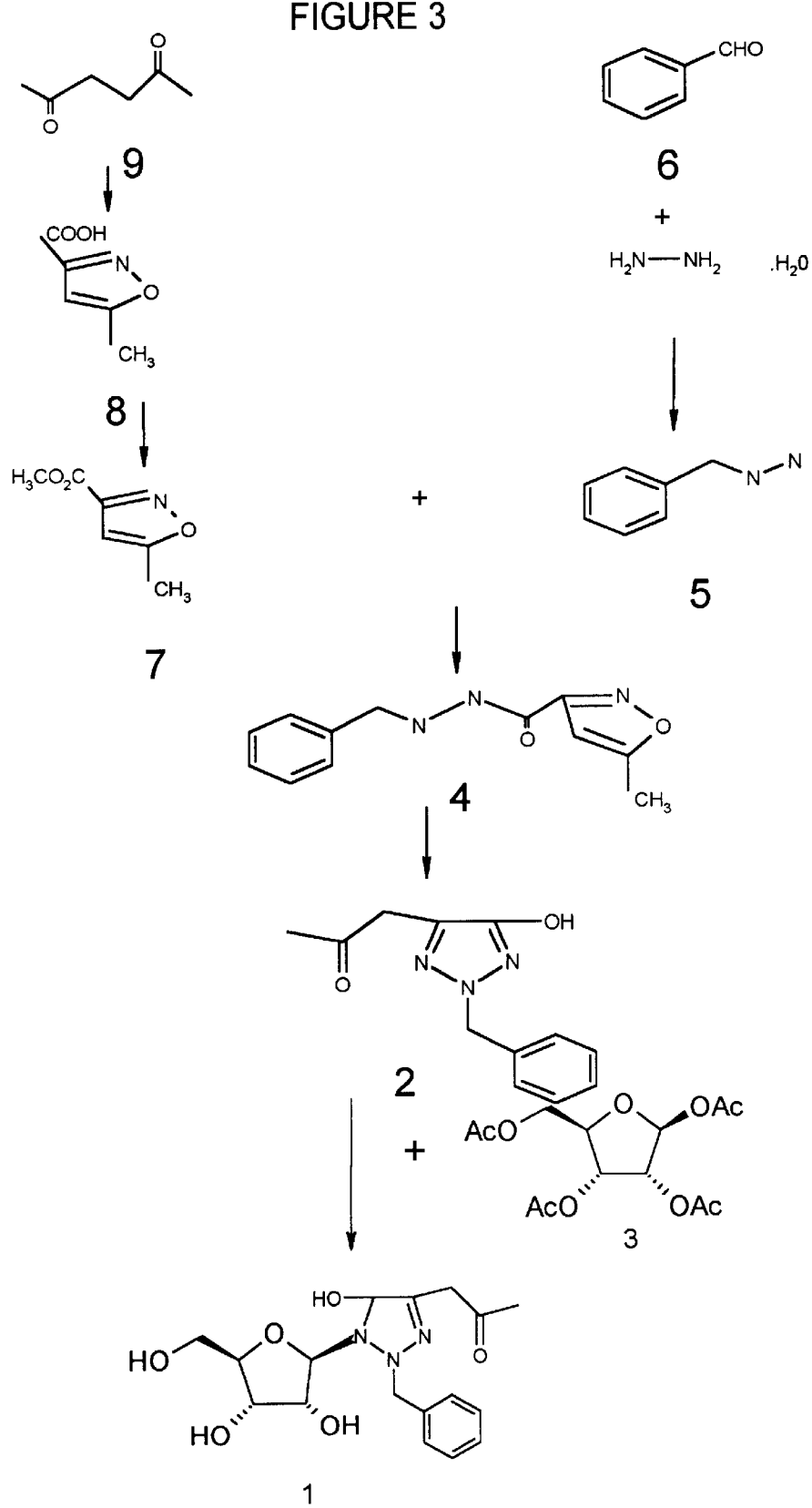
FIG. 3 represents the entire reaction scheme to produce the ribonucleoside TRIBOSE 1. The reaction to form the ribonucleoside 1 can be carried out either chemically or enzymatically (published examined Japanese patent application No. 17830/79, and published unexamined Japanese patent application nos. 146593/82, 190396/83, 216696/83, 6895/84, 143599/84). The preceding referenced methods used to prepare Ribavirin parallel the methods that can be utilized producing TRIBOSE, namely a fermentation method which comprises culturing a microorganism in a medium containing the 1,2,3 triazole described to form TRIBOSE 1, and an enzymatic method which comprises allowing a microorganism cell to act on the 1,2,3 triazole described and a ribose donor to produce TRIBOSE 1.
Figure 4:
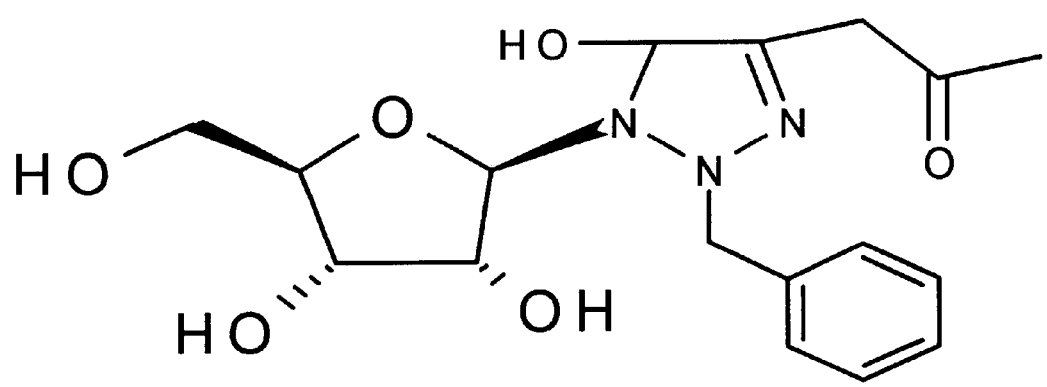
FIG. 4 represents the current invention TRIBOSE 1 and the various substituents on the triazole ring representing derivatives as described to form 1A.
Figure 4:
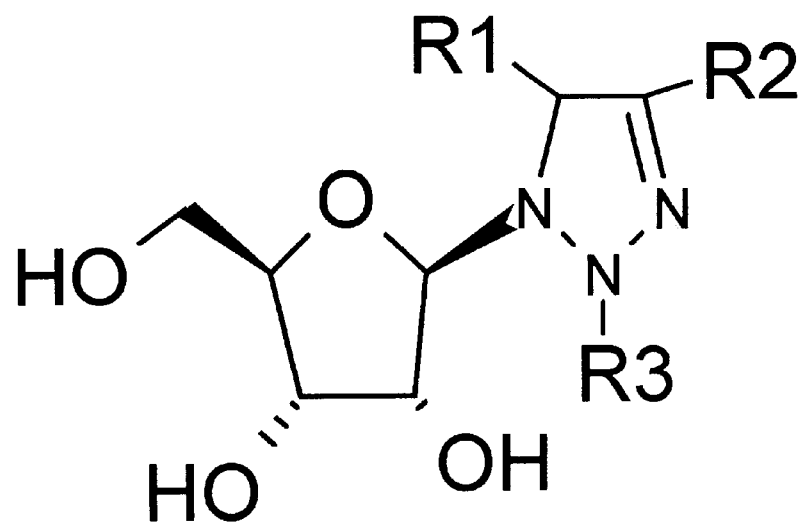

What is not shown in order to simplify the description of the invention is the protection and deprotection of the ribose entity which is accomplished through either acetyl, triphenylacetyl, phosphoryl, silyloxymethyl, or other such protection groups described in the literature (U.S. Pat. Nos. 3,976,545, 3,798,209, 4,614,719), and textbooks such as Protective Groups in Organic Synthesis, Greene, John Wiley and Sons, NY (1981). The protecting groups are added and removed by conventional chemical techniques well known to a skilled person. Additionally, the Ribose donor can be D-Ribose or various phosphoric esters thereof. It also does not matter whether such a Ribonucleoside is derived from a naturally occurring product or from a chemical synthesis. The phosphates of the Ribonucleoside may have a monophosphate, diphosphate or triphosphate moiety at one two or all of the 2,3,and 5, positions

OVERVIEW DESCRIPTION OF THE INVENTION

The synthesis of the novel compound TRIBOSE 1 starts with commercially available raw materials and uses established chemistry to form the intermediate 3-Isoxazolecarboxylic acid, 5-methyl-,2-(phenylmethyl)-hydrazide. The subsequent reactions to form the nucleoside represents new chemistry not previously reported. The formation of TRIBOSE 1 from this nucleoside by reacting it with a suitably protected ribose has also been previously described in regard to other ribonucleosides but the formation of the ribonucleoside TRIBOSE 1 is unique.

2,5-Hexanedione, 9 is the starting material for the process. 2,5-Hexanedione 9 is nitrated and oxidized with nitric acid to form 5-methyl-3-isoxazolecarboxlic acid 8, (isoxazole acid). Isoxazole acid 8 is esterified by treating it with methyl alcohol and sulfuric acid to give 5-methyl-3-isoxazolecarboxylic acid methyl ester, isoxazole ester 7. Isoxazole ester 7 is reacted with Benzylhydrazine 5 which itself is prepared from the reaction of benzaldehyde 6 with hydrazine and then reduced with hydrogen to form Benzylhydrazine 5.

The reaction of isoxazole ester 7 with Benzylhydrazine 5 results in the formation of 3-Isoxazolecarboxylic acid, 5-methyl-,2-(phenylmethyl)-hydrazide 4. The hydrazide 4 is thermally isomerized to form the nucleoside 1,2,3 triazole 2. 1,2,3 triazole 2 is reduced and reacted with a suitably protected D-ribose, and deprotected to form the novel ribonucleoside TRIBOSE 1.

Reaction of the trimethylsilyl derivative of the triazole nucleoside 2 with O-Acetyl protected D-Ribose 3 to form the new protected ribonucleoside TRIBOSE 1 is carried out in acetic acid at room temperature. Deacylation using sodium methoxide in methanol or methanolic ammonia afforded TRIBOSE 1.

The ribose donor can be any one of Ribonucleosides or D-ribose or various phosphoric esters thereof. It can be derived from a naturally occurring product or from a chemical synthesis. The ribose phosphates can either be in the free form or conventional alkali salts such as sodium, potassium, calcium etc.

DETAILED DESCRIPTION OF THE INVENTION

A solution of 65 g of nitric acid in 77 ml of water is heated to reflux and 25 g of acetonylacetone 9 is added at a rate to maintain reflux. After the addition is complete, reflux is continued for an additional 2 hours. The mixture is cooled to 10 degrees C. and diluted with 77 ml of water to precipitate isoxazole acid 8, which is filtered, washed with 25 ml of water and vacuum dried at 60 degrees C. to afford 15 g of 5-Methyl-3-isoxazolecarboxylic acid 8.

40 g of 5-Methyl-3-isoxazolecarboxylic acid 8 is dissolved in 80 ml of methanol and esterified by adding 8 ml of sulfuric acid to the reaction mixture at 45 degrees C. The solution is cooled to 30 degrees C., diluted with 60 ml of water and neutralized with 14 g of aqueous ammonium hydroxide. The reaction mixture is cooled to 10 degrees C. and the resulting slurry of crystals is filtered, washed with 60 ml of water and vacuum dried at 40 degrees C. overnight to afford 40 g of isoxazole ester 7.

32 g of Benzaldehyde 6 is treated with 17.7 g of 85% hydrazine hydrate in 25 ml of isopropyl alcohol for one-half hour at 60 degrees C. to form the shiff base, which is reduced with hydrogen under pressure with palladium on carbon catalyst at 55 degrees C. until the hydrogen uptake stops. After filtering off the catalyst. the resulting solution is concentrated to form 35 g of benzylhydrazine 5.

The benzylhydrazine 5 is reacted with th, isoxazole ester 7 described above by dissolving 40 g of the ester in 60 g of isopropanol and adding 35 g of benzylhydrazine 5. The reaction solution is heated to 45 degrees C. and allowed to agitate for 60 hours. After cooling to 10 degrees C., The resulting crystals are filtered off and washed with 20 ml of cold isopropanol and vacuum dried at 45 degrees C. for 24 hours to produce 25 g of 3-Isoxazolecarboxylic acid, 5-methyl-,2-(phenylmethyl)-hydrazide 4.

25 g of 3-Isoxazolecarboxylic acid, 5-methyl-,2-(phenylmethyl)-hydrazide 4 is thermally isomerized by refluxing in 120 g of toluene overnight to form the 1,2,3-triazole nucleoside 2. The toluene solution is vacuum concentrated and cooled to 25 degrees C. The resulting slurry of crystals is filtered off and washed with toluene to afford 16 g of the triazole 2.

8 g of the triazole 2 is reacted with excess hexamethyldisilazane at reflux to form the trimethylsilyl derivative of the triazole 2. The resulting reaction solution is evaporated to dryness and reacted with 18 g of the O-acetyl derivative of D-Ribose in acetonitrile at room temperature. The solvent is evaporated to dryness and the residue dissolved in methylene chloride. After purification by silica gel column chromatography, the resulting product is deprotected by reaction with methanolic ammonia at room temperature. The solution is concentrated to dryness and the residue crystallized from ethanol-ethyl acetate to yield 3 g of the triazole 1.

I claim:

1. A compound of formula 1

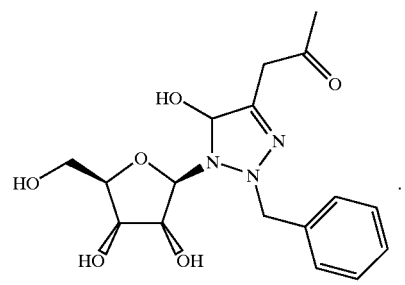

Formula 1

2. A process for preparing the compound of formula 2

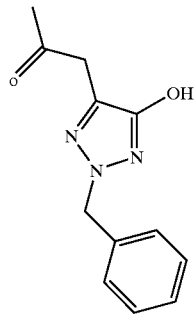

Formula 2 by the thermal isomerization of the compound of formula 4.

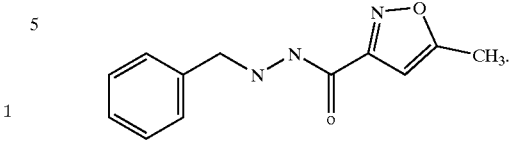

Formula 4

3. The compound of formula 1A

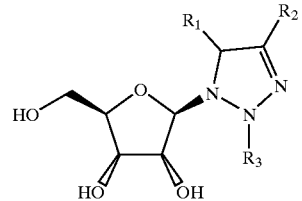

Formula 1A wherein $R_1$, $R_2$ and $R_3$ are selected from the group consisting of alkyl, acyl, hydroxy, amino or phenyl and wherein $R_2$ can also be 2-oxo-propyl and wherein $R_3$ can also be phenylmethyl.

4. The compound of formula 2

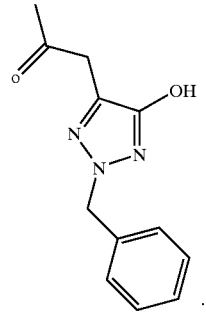

Formula 2

* * * * *